United States Patent
Higashiyama et al.

(10) Patent No.: US 6,746,857 B2
(45) Date of Patent: Jun. 8, 2004

(54) MEDIA FOR CULTURING MICROORGANISMS AND PROCESS FOR PRODUCING UNSATURATED FATTY ACIDS OR LIPIDS CONTAINING THE SAME

(75) Inventors: Kenichi Higashiyama, Osaka (JP); Toshiaki Yaguchi, Osaka (JP); Kengo Akimoto, Osaka (JP); Sakayu Shimizu, Kyoto (JP)

(73) Assignee: Suntory Limited, Osaka (JP)

(*) Notice: Subject to any disclaimer, the term of this patent is extended or adjusted under 35 U.S.C. 154(b) by 0 days.

(21) Appl. No.: 09/331,759

(22) PCT Filed: Dec. 26, 1997

(86) PCT No.: PCT/JP97/04898

§ 371 (c)(1),
(2), (4) Date: Jun. 25, 1999

(87) PCT Pub. No.: WO98/29558

PCT Pub. Date: Jul. 9, 1998

(65) Prior Publication Data

US 2001/0016342 A1 Aug. 23, 2001

(30) Foreign Application Priority Data

Dec. 27, 1996 (JP) .............................. 8-349541

(51) Int. Cl.⁷ ................................. C12P 7/64
(52) U.S. Cl. .................... 435/134; 435/135; 435/253.6; 435/254.1
(58) Field of Search ................ 435/134, 135, 435/253.6, 254.1

(56) References Cited

U.S. PATENT DOCUMENTS

| 4,783,408 A | * | 11/1988 | Suzuki | 435/134 |
| 5,015,579 A | * | 5/1991 | Yamaguchi | 435/123 |
| 5,026,644 A | * | 6/1991 | Manoh | 435/134 |

FOREIGN PATENT DOCUMENTS

| JP | 52-64484 | 5/1977 |
| JP | 57-144986 | 9/1982 |
| JP | 59-130191 | 7/1984 |
| JP | 60-126091 | 7/1985 |
| JP | 63-12290 | 1/1988 |
| JP | 63-14696 | 1/1988 |
| JP | 63-14697 | 1/1988 |
| JP | 63-133994 | 6/1988 |
| JP | 63-240791 | 10/1988 |
| JP | 1-199588 | 8/1989 |
| JP | 2-86789 | 3/1990 |
| JP | 3-49688 | 3/1991 |
| JP | 5-91888 | 4/1993 |
| JP | 8-214893 | 8/1996 |

OTHER PUBLICATIONS

Sigma Cell Culture Reagents Catalogue, pp. 282 and 286 (1992).

* cited by examiner

*Primary Examiner*—Irene Marx
(74) *Attorney, Agent, or Firm*—Burns, Doane, Swecker & Mathis, L.L.P.

(57) ABSTRACT

A process for controlling the mycelial morphology of a microorganism belonging to the genus Mortierella during culturing and a process for producing unsaturated fatty acids and a lipid containing them by using a culture medium for culturing a microorganism in which phosphate ions, potassium ions, sodium ions, magnesium ions, and calcium ions in the culture medium are in the range of 5 to 60 mM, 5 to 60 mM, 2 to 50 mM, 0.5 to 9 mM, and 0.5 to 12 mM, respectively, characterized in that the microorganism belonging to the genus Mortierella is cultured in a culture medium containing phosphate ions in the range of 5 to 60 mM, potassium ions in the range of 5 to 60 mM, sodium ions in the range of 2 to 50 mM, magnesium ions in the range of 0.5 to 9 mM, and calcium ions in the range of 0.5 to 12 mM, respectively, to produce unsaturated fatty acids and the lipid containing them, and the culture medium for culturing a microorganism having phosphate ions, potassium ions, sodium ions, magnesium ions, and calcium ions in the range of 5 to 60 mM, 5 to 60 mM, 2 to 50 mM, 0.5 to 9 mM, and 0.5 to 12 mM, respectively.

14 Claims, No Drawings

MEDIA FOR CULTURING MICROORGANISMS AND PROCESS FOR PRODUCING UNSATURATED FATTY ACIDS OR LIPIDS CONTAINING THE SAME

TECHNICAL FIELD

The present invention relates to a novel culture medium for culturing a microorganism, and a process of producing an unsaturated fatty acid-containing lipid that can be obtained by culturing a microorganism belonging to the genus Mortierella capable of producing unsaturated fatty acids in said medium.

BACKGROUND ART

Arachidonic acid, dihomo-γ-linolenic acid, eicosapentaenoic acid, Mead acid and the like are said to be precursors of prostaglandins, thromboxanes, prostacyclins, leukotrienes and the like that have potent and a variety of biological activities, and thereby are attracting much attention in recent years. For example, a rapid progress has been made on the study of arachidonic acid, as of docosahexaenoic acid (DHA) as a ingredient essential especially for the growth of infants; Lanting et al. have carried out a follow-up study on infants bred with breast milk and those bred with infant formula for three weeks or longer after birth until they grew up to the age of nine years old for the incidence of minor disorders in the cerebral nerves based on their behavioral aspects etc. and have reported that the incidence of cerebral disorders in the children bred with infant formula is twice as high as that of the children bred with breast milk (LANCET, vol. 344, 1319–1322 (1994)).

It has been speculated that this shocking result is due to the possibility that such unsaturated fatty acid as DHA and arachidonic acid that are present in the breast milk but not in the infant formula may be associated with the development of the brain. Since then, many reports have appeared that suggest the association of unsaturated fatty acids with the development of the infant's brain and retina, which is attracting attention as the latest topic in the field of nutrition for preterms and newborns.

These unsaturated fatty acids widely occur in the animal kingdom: for example, arachidonic acid has been isolated from a lipid that was extracted from the adrenal gland or the liver of animals. The content of unsaturated fatty acids therein, however, is low and was insufficient for its large scale supply, and therefore various methods have been devised to obtain unsaturated fatty acids by culturing various microorganisms. Among others, microorganisms belonging to the genus Mortierella are known to produce unsaturated fatty acids such as arachidonic acid, dihomo-γ-linolenic acid, eicosapentaenoic acid, Mead acid and the like and thus methods have been developed that produce said unsaturated fatty acids by the fermentation method using these microorganisms (Japanese Unexamined Patent Publication (Kokai) No. 63(1988)-44891, Japanese Unexamined Patent Publication (Kokai) No. 63(1988)-12290, Japanese Unexamined Patent Publication (Kokai) No. 63(1988)-14696, and Japanese Unexamined Patent Publication (Kokai) No. 63(1988)-14697).

There is also known a method of producing Mead acid using a mutant strain in which the Δ12 desaturating activity has been reduced or defected that can be obtained by subjecting an organism of the genus Mortierella to a mutation treatment (Japanese Unexamined Patent Publication (Kokai) No. 5(1993)-91888). Furthermore, there is also known a method of producing dihomo-γ-linolenic acid using a mutant strain in which the Δ5 desaturating activity has been reduced or defected that can be obtained by subjecting an organism of the genus Mortierella to a mutation treatment (Japanese Unexamined Patent Publication (Kokai) No. 5(1993)-91887).

However, when a fermentation production is carried out in a liquid medium using a filamentous fungus like the genus Mortierella, cellular growth often results in the enhanced viscosity of the liquid culture medium and the ensuing reduced supply of oxygen. Although a method (Japanese Unexamined Patent Publication (Kokai) No. 6(1994)-153970) of regulating dissolved oxygen developed to overcome the above drawbacks has played an important role in enhancing productivity, it is not sufficient to attain high productivity that is economically excellent on an industrial scale. Thereby, the extensive development of culture techniques including the search for more inexpensive culture medium and trace nutrients, the method of regulating mycelial morphology to improve fluidity of the liquid culture medium is imperative.

As a strategy for such technological development, the effect of adding salts as trace nutrients on mycelial morphology are being investigated. There are various reports on effect of adding ions such as potassium, sodium, calcium, magnesium, and phosphoric acid among others (International Application WO96/21037, Japanese Unexamined Patent Publication (Kokai) 8(1996)-214893, Appl. Microbiol. Biotechnol., Vol. 39, p. 450 (1993), Biotechnology Lett., Vol. 12, No. 6, p. 455 (1990), Yukagaku (Oil Chemistry) Vol. 37, No. 3, p. 241 (1989), Yukagaku (Oil Chemistry) Vol. 42, No. 11, p. 893 (1993)). On the other hand, however, there are no reports that investigated the effect of more aggressively enhancing the productivity of unsaturated fatty acids by adding these major ions at concentrations of 0.5 mM or higher exceeding the concept of being nutritional supplements and no reports that even investigated the effects which the balance of added ions has on mycelial morphology and lipid compositions. It is, therefore, desired to optimize the method of adding ions.

DISCLOSURE OF THE INVENTION

Thus, it is an object of the present invention to provide a process of producing a lipid containing unsaturated fatty acids by a fermentation of microorganism belonging to the genus Mortierella, said process comprising adding salts to the culture medium to improve the productivity of unsaturated fatty acids, more specifically all of microbial growth, the accumulation of unsaturated fatty acids, and the accumulation of total lipids, and thereby attaining an economical and stable supply of the lipid containing unsaturated fatty acids. It is also an object of the present invention to provide a culture medium for culturing a microorganism that has an advantage of producing unsaturated fatty acids at high yields and that is inexpensive.

In order to solve the above problems, the present inventors have carried out a comprehensive study concerning the effects of adding salts to a culture medium with respect to not only the yield of unsaturated fatty acids but also changes in mycelial morphology and lipid composition. As a result, the inventors have found that it is very effective to add all the ions of potassium, sodium, calcium, magnesium, and phosphate at defined concentrations in a well-balanced manner and thereby have completed the present invention.

Thus, the present invention provides a culture medium for culturing a microorganism in which phosphate ions, potassium ions, sodium ions, magnesium ions, and calcium ions are in the range of 5 to 60 mM, 5 to 60 mM, 2 to 50 mM, 0.5 to 9 mM, and 0.5 to 12 mM, respectively, and a process having an enhanced productivity of producing unsaturated fatty acids and a lipid containing the same by culturing in said medium a filamentous fungus in particular a microorganism belonging to the genus Mortierella.

The term "unsaturated fatty acids" as used herein refers to the fatty acids having 16 or more carbon atoms and one or more double bonds. Among these, those having 18 or more carbon atoms and two or more double bonds are generally called highly unsaturated fatty acids, which for example include γ-linolenic acid, dihomo-γ-linolenic acid, arachidonic acid, eicosapentaenoic acid, Mead acid, 6,9-octadecadienoic acid, 8,11-eicosadienoic acid and the like.

Embodiment for Carrying Out the Invention

The culture medium for culturing a microorganism of the present invention contains phosphate ions, potassium ions, sodium ions, magnesium ions, and calcium ions in the range of 5 to 60 mM, 5 to 60 mM, 2 to 50 mM, 0.5 to 9 mM, and 0.5 to 12 mM, respectively, preferably in the range of 10 to 45 mM, 10 to 45 mM, 5 to 40 mM, 1 to 6 mM, and 1 to 9 mM, respectively, and can be used for culturing a microorganism for example a filamentous fungus.

In the case of a microorganism belonging to genus Mortierella capable of producing unsaturated fatty acids, the unsaturated fatty acids can be obtained at a high yield from the culture by using the culture medium of the present invention. The culture medium of the present invention may contain, as appropriate, ingredients such as a carbon source, a nitrogen source, a trace nutrient source etc. in addition to phosphate ions, potassium ions, sodium ions, magnesium ions, and calcium ions depending on the microorganism to be used.

According to the present invention, microorganisms used in the production of a lipid containing unsaturated fatty acids may be any organism belonging to genus Mortierella. For example, these microorganisms include such microbial strains as are described in MYCOTAXON, Vol. XLIV, No. 2, pp. 257–265 (1992), and more specifically include microorganisms belonging to the subgenus Mortierella such as *Mortierella elongata* IFO 8570, *Mortierella exigua* IFO 8571, *Mortierella hygrophila* IFO 5941, *Mortierella alpina* IFO 8568, ATCC 16266, ATCC 32221, ATCC 42430, CBS 219.35, CBS 224.37, CBS 250.53, CBS 343.66, CBS 527.72, CBS 528.72, CBS 529.72, CBS 608.70, and CBS 754.68; and microorganisms belonging to the subgenus Micromucor such as *Mortierella isabellina* CBS 194.28, IFO 6336, IFO 7824, IFO 7873, IFO 7874, IFO 8286, IFO 8308, IFO 7884, *Mortierella nana* IFO 8190, *Mortierella ramanniana* IFO 5426, IFO 8186, CBS 112.08, CBS 212.72, IFO 7825, IFO 8184, IFO 8185, IFO 8287, and *Mortierella vinacea* CBS 236.82.

These microbial strains are all available without limitation from the Institute for Fermentation, Osaka, in Japan, the American Type Culture Collection (ATCC) in the USA, and the Centraalbureau voor Schimmelcultures (CBS) in the Netherlands. Furthermore, the microbial strain *Mortierella elongata* SAM 0219 (FERM P-8703) (FERM BP-1239) that was isolated from the soil by the inventors may be used. These microbial strains belonging to type cultures and microbial isolants isolated from the nature can be used as they are, and there can also be used spontaneous mutants that were obtained by effecting growth and/or isolation once or more and that have a property different from the original microbial strain.

Microorganisms for use in the present invention can include the mutants and recombinants of the organisms belonging to the genus Mortierella (wild type strain), that is, the organisms intended and designed to produce an increased amount of specific and/or all unsaturated fatty acids in a lipid or an increased amount of total lipids, or an increased amount of both of them in comparison with an amount produced by the original wild type strain when cultured in the same medium. For example, as a mutant that was designed to produce an increased amount of specific unsaturated fatty acids, there can be mentioned *Mortierella alpina* SAM 1861 (FERM BP-3590) in which the Δ12-desaturating activity has been defected, and *Mortierella alpina* SAM 1860 (FERM BP-3589) in which the Δ5-desaturating activity has been defected.

Furthermore, there is also included a microorganism that was designed to produce unsaturated fatty acids at an amount equal to that of the corresponding wild type strain using a substrate having a better cost performance in an efficient manner.

Microorganisms belonging to the above genus Mortierella can be cultured according to a conventional method except that the concentrations of phosphate ions, potassium ions, sodium ions, magnesium ions, and calcium ions in the culture medium are adjusted to be in their specific range. For example, the above-mentioned microorganisms in the form of spores, hypha, or liquid preculture obtained by culturing in advance are inoculated and cultured on a liquid culture medium or a solid culture medium. As the carbon source, any of the commonly used glucose, fructose, xylose, saccharose, maltose, soluble starch, molasses, glycerol, mannitol, citric acid, corn starch, and the like can be used, and in particular glucose, maltose, fructose, corn starch, glycerol, and citric acid are preferred.

As the nitrogen source, organic nitrogen sources such as peptone, yeast extract, malt extract, meat extract, casaminic acid, corn steep liquor, urea, and the like and inorganic nitrogen sources such as ammonium nitrate, ammonium sulfate, and the like can be used. In particular, by using one or more nitrogen sources obtained from soy beans alone or in combination with the above nitrogen sources, a more preferred synergistic effect of adding salts can be obtained.

Furthermore, as the nitrogen source derived from soy beans, defatted soy beans or defatted soy beans that were subjected to a heat treatment; an acid treatment; an alkali treatment; an enzyme treatment; a chemical modification; or denaturation and/or renaturation using a chemical and/or physical treatment comprising any of the above treatments; the removal of some of the components with water and/or an organic solvent; the removal of some of the components by filtration and/or centrifugation; freezing; disrupting; drying; and/or sieving and the like; or non-defatted soy beans that were subjected to the same treatment as above can be used either alone or in combinations. In general, there can be mentioned soy beans, defatted soy beans, soy bean flakes, edible soy bean proteins, bean curd lees (okara), soy bean milk, roasted soy bean flour (kinako), and the like. Preferably the defatted soy beans that were subjected to a heat treatment, and more preferably the defatted soy beans that were subjected to a heat treatment at about 70–90° C. followed by the removal of the ethanol-soluble components are used.

In addition to phosphate ions, potassium ions, sodium ions, magnesium ions, and calcium ions, there can be used, when desired, as a source of trace nutrient, metal ions such as iron ions, copper ions, zinc ions, manganese ions, nickel ions, and cobalt ions, and vitamins and the like. In order to increase the yield of unsaturated fatty acids, there can be used, as a precursor to unsaturated fatty acids, hydrocarbon such as hexadecane or octadecane; fatty acids such as oleic acid or linoleic acid or salts thereof, or fatty acid esters such as ethylester, glycerol fatty acid ester, and sorbitan fatty acid ester; or lipids such as olive oil, soy bean oil, rapeseed oil, cotton seed oil, or coconut oil can be used either alone or in combination. The amount of the substrate added is 0.001 to 10%, preferably 0.5 to 10%. In addition culturing may be carried out using one of these substrates as the sole carbon source.

In the culture medium of the present invention, phosphate ions are present in the range of 5 to 60 mM, potassium ions in the range of 5 to 60 mM, sodium ions in the range of 2 to 50 mM, magnesium ions in the range of 0.5 to 9 mm, and calcium ions in the range of 0.5 to 12 mM, and preferably, in the culture medium, phosphate ions are in the range of 10 to 45 mM, potassium ions are in the range of 10 to 45 mM, sodium ions are in the range of 5 to 40 mM, magnesium ions are in the range of 1 to 6 mM, and calcium ions are in the range of 1 to 9 mM.

These ions can be prepared by adding to the culture medium salts such as dipotassium hydrogen phosphate, potassium dihydrogen phosphate, disodium hydrogen phosphate, and/or sodium dihydrogen phosphate for phosphate ions, salts such as dipotassium hydrogen phosphate, potassium dihydrogen phosphate and/or potassium chloride for potassium ions, salts such as disodium hydrogen phosphate, sodium dihydrogen phosphate, sodium chloride and/or sodium sulfate for sodium ions, salts such as magnesium chloride and/or magnesium sulfate for magnesium ions, and salts such as calcium chloride and/or calcium carbonate for calcium ions. However, these compounds are not limiting and any compound can be used as long as it does not inhibit the growth of microorganisms.

These salts may be either hydrates or anhydrides. Furthermore, the salts described above are combined, as appropriate, so as to obtain the ion concentrations in the range of the present invention. For example, by blending certain amounts of 4 compounds such as potassium dihydrogen phosphate ($KH_2PO_4$), anhydrous sodium sulfate ($Na_2SO_4$), magnesium chloride hexahydrate ($MgCl_2.6H_2O$), and calcium chloride dihydrate ($CaCl_2.2H_2O$), certain concentrations of ions of the present invention can be prepared.

According to the present invention, the addition of such salts substantially increases the yield of unsaturated fatty acids. Furthermore, although their effects on mycelial morphology in the liquid culture cannot be specified because of the effects from components other than the salts of the medium and from microbial strains, an increased amount of the phosphate added results in an increased proportion of the mycelia in the pulp form, and an increased amount of magnesium added results in an increased proportion of the mycelia in the pellet form. Growth in the pulp form increases the viscosity of the liquid culture medium and reduces fluidity and the concentration of dissolved oxygen, thereby causing a reduction in the yield.

Growth in the pellet form, on the other hand, seldom results in an increase in viscosity and thereby a high fluidity is maintained, but the pellet wall provides a rate-liming factor of oxygen supply and causes a reduction in the yield. We have found, however, that by adding said ions at certain concentrations in a well-balanced manner, excessive pulp-formation and excessive pellet-formation can be controlled and the mixed state of the pulp and the pellets can be maintained. This technique has enabled it easy to control mycelia morphology and to obtain very high yields.

The lipid containing unsaturated fatty acids obtained as described above are mostly triglycerides, and the percentage of phospholipid increases with an increase in the amount of phosphate added to the medium. We have discovered, however, that by adding potassium ions, sodium ions, magnesium ions, calcium ions in addition to phosphate ions in a well-balanced manner the percentage of the triglycerides in the microbial lipids can be maintained at 90% or higher. When the target lipid is triglycerides, high recovery can be maintained by mixing the added salts in a well-balanced manner within the ranges as specified herein.

The above carbon source, nitrogen source, and other components of the medium can be added to the culture medium before culturing and/or to the liquid culture medium during culturing. These components of the culture medium can be added at one time or sequentially, or in several portions over time. These components of the culture medium can be sterilized and added alone or after mixing, and the method of sterilization or the order of adding are not particularly limited. Preferably the carbon source and the nitrogen source are separately sterilized, and the salts are added by the end of the logarithmic growth, more preferably before the middle of the logarithmic growth. The concentrations of the other components of the culture medium that do not affect the concentrations of phosphate ions, potassium ions, sodium ions, magnesium ions, and calcium ions are not limited so long as they do not inhibit the growth of the microorganism.

Practically, the total amount of the carbon source to be added is in general 0.1 to 40% by weight, preferably 1 to 25% by weight, the total amount of the nitrogen source to be added is 0.01 to 10% by weight, preferably 0.1 to 10% by weight, and more preferably the initial amount of the carbon source to be added is 1 to 5% by weight and that of the nitrogen source to be added is 0.1 to 6% by weight, and during culturing the carbon source and the nitrogen source, more preferably the carbon source alone, are added and cultured. The culturing temperature is 5 to 40° C., preferably 20 to 30° C. Furthermore, it is also possible to produce unsaturated fatty acids by growing the microbial cells at 20 to 30° C. followed by culturing at 5 to 20° C. to produce unsaturated fatty acids.

The pH of the culture medium is 4 to 10, preferably 5 to 8, and an aeration and agitation culture, a shaking culture, or a stationary culture is carried out. The culturing is generally continued for 2 to 20 days. By culturing in this way, a lipid containing unsaturated fatty acids is formed and accumulated in the microbial cells. In the production of unsaturated fatty acids, the aeration and agitation culture with a liquid culture medium is preferred.

The desired lipid can be obtained by a conventional method from the liquid culture medium in the middle of producing the lipid by culturing or the sterilized liquid culture medium thereof, or from the liquid culture medium after the completion of culturing or the sterilized liquid culture medium thereof, or the cultured microbial cells collected from the respective cultures or the dried products thereof. From the cultured microbial cells, the desired lipid can be obtained, for example, by the following method.

After culturing is over, the cultured microbial cells can be obtained from the liquid culture medium by a conventionally used method of separating the solid from the liquid such as centrifugation and/or filtration. The cultured microbial cells are preferably washed with water, disrupted, and dried.

Drying is effected by lyophilization, air-drying, and the like. The dried microbial cells are subjected to extraction with an organic solvent preferably under a stream of nitrogen. As an organic solvent, ether, hexane, methanol, ethanol, chloroform, dichloromethane, petroleum ether and the like can be used, and satisfactory results can be also obtained by an alternate extraction with methanol and petroleum ether or a single-layer solvent comprising chloroform-methanol-water, and preferably extracted with hexane.

By evaporating the organic solvent from the extract under reduced pressure, a high concentration of a lipid containing unsaturated fatty acids can be obtained. The above method can be replaced with extraction using the wet microbial cells. In this case, a water-miscible solvent such as methanol or ethanol, or a mixture of these solvents with water and/or other solvents are used. The other procedures are the same as described above. The unsaturated fatty acids-containing triglycerides from the unsaturated fatty acids-containing lipid collected from the culture can be separated and purified according to a conventional means such as solvent extraction, the removal of the solvent, followed by deacidification, decolorization, deodorization, degumming, or refrigerated centrifugation and the like.

phosphate alone was added, no increase was noted in the amount of arachidonic acid produced.

In addition to the amount of arachidonic acid produced, the amount of each component was quantitated using the TLC/FID analyzer (Iatroscan manufactured by Iatron) after the lipid was extracted with hexane from the microbial cells obtained followed by the fractionation of lipid by the TLC method under a separation condition of hexane: diethylether: formic acid=42:28:0.3.

As a result, it was found that the addition of potassium hydrogen phosphate alone resulted in an increase in the percentage of phospholipids in the lipid of the microbial cells extracted with hexane, and, on the other hand, the addition of all four kinds of salts including potassium hydrogen phosphate produced the lipid composition similar to that obtained with no addition of salts, thereby confirming that the addition of all ions in a well-balanced manner gives lipids with a high triglyceride content when the desired product is triglyceride.

TABLE 1

| Culture medium | Yeast extract 1% | Soy Bean protein 1.5% | Yeast extract 1% $KH_2PO_4$ 0.3% (22 mM) $MgCl_2.6H_2O$ 0.05% (2.5 mM) $Na_2SO_4$ 0.1% (7.0 mM) $CaCl_2.2H_2O$ 0.05% (3.4 mM) | Soy bean protein 1.5% $KH_2PO_4$ 0.3% (22 mM) $MgCl_2.6H_2O$ 0.05% (2.5 mM) $Na_2SO_4$ 0.1% (7.0 mM) $CaCl_2.2H_2O$ 0.05% (3.4 mM) | Soy bean protein 1.5% $KH_2PO_4$ 0.3% (22 mM) |
| --- | --- | --- | --- | --- | --- |
| Amount of arachidonic acid produced | 2.28 g/L | 1.93 g/L | 3.07 g/L | 3.24 g/L | 2.00 g/L |
| Amount of total lipid produced | 6.57 g/L | 5.74 g/L | 8.82 g/L | 8.95 g/L | 5.83 g/L |
| Concentration of dry microbial cells | 17.3 g/L | 15.7 g/L | 19.3 g/L | 22.0 g/L | 16.0 g/L |
| Content of triglyceride | 97.2% | 97.4% | 97.0% | 96.0% | 88.3% |
| Content of phospholipid | 1.2% | 1.2% | 1.4% | 1.2% | 9.5% |

Yeast extract: manufactured by Universal Foods, TASTONE154AG
Soy bean protein: tread name; Esusan Meat, product of Ajinomoto Co. Ltd.

EXAMPLES

The present invention will now be explained in further details with reference to the following examples.

Example 1

*Mortierella alpina* CBS 754.68 was used as an arachidonic acid-producing microorganism. Each of four culture media containing 2% of glucose, 0.1% of soy bean oil, and the nitrogen source and salt components described in Table 1 in 5 liters was prepared in a 10-liter fermentor, and the initial pH was adjusted to 6.0. Fifty ml of the liquid preculture was inoculated and an aeration/agitation culture was carried out for 8 days at 28° C., an aeration rate of 1.0 vvm and an agitation speed of 300 rpm. The glucose concentration was maintained at between 1% and 2% by fed-batch method till day 4, and at between 0.5% and 1% thereafter.

As a result of culturing, it was found that the amount of arachidonic acid produced increased by 1.35 fold when all 5 ions were added to the yeast extract medium and by 1.68 fold when added to soy bean protein, confirming the effectiveness of the addition of salts. When potassium hydrogen Example 2

*Mortierella alpina* CBS 754.68 was used as an arachidonic acid-producing microorganism. Each of four culture media containing 2% glucose, 1.5% roasted soy bean flour (kinako), 0.1% soy bean oil and the salts shown in Table 2 in 25 liters was prepared in a 50-liter fermentor, and the initial pH was adjusted to 6.2. Fifty milliliters of the liquid precultrue was inoculated thereinto and then was subjected to an aeration/agitation culture at 28° C., an aeration rate of 1.0 vvm, an agitation speed of 300 rpm, and a fermentor internal pressure of 200 kPa for 8 days. The glucose concentration was maintained at between 1% and 2% using fed-batch method till day 4 and at 0.5% and 1% thereafter.

After culturing, the production of arachidonic acid increased by the addition of salts, confirming the effectiveness of salt addition and the effective concentration ranges.

TABLE 2

| Amount of $KH_2PO_4$ added | 0% | 0.075% (5.5 mM) | 0.3% (22 mM) | 1.2% (88 mM) |
| --- | --- | --- | --- | --- |
| Amount of $MgCl_2.6H_2O$ added | 0% | 0.0125% (0.61 mM) | 0.05% (2.5 mM) | 0.2% (9.8 mM) |
| Amount of $Na_2SO_4$ | 0% | 0.025% | 0.1% | 0.4% |

TABLE 2-continued

| added | | (1.8 mM) | (7.0 mM) | (28 mM) |
|---|---|---|---|---|
| Amount of $CaCl_2.2H_2O$ added | 0% | 0.0125% (0.85 mM) | 0.05% (3.4 mM) | 0.2% (14 mM) |
| Amount of arachidonic acid produced | 2.11 g/L | 2.61 g/L | 2.90 g/L | 1.95 g/L |

Example 3

*Mortierella alpina* CBS 754.68 was used as an arachidonic acid-producing organism. Each of four culture media containing 2% glucose, 1.5% defatted soy powder, 0.1% soy bean oil and the salts shown in Table 3 in 25 liters was prepared in a 50-liter fermentor, and the initial pH was adjusted to 6.0. Fifty milliliters of the liquid precultrue was inoculated thereinto and then was subjected to an aeration/agitation culture at 28° C., an aeration rate of 1.0 vvm, an agitation speed of 300 rpm, and a fermentor internal pressure of 200 kPa for 8 days. The glucose concentration was maintained at between 1% and 2% using fed-batch method till day 4 and at between 0.5% and 1% thereafter.

In the salt-free culture medium, the microorganisms propagated with the mycelial morphology at a mixed state of the pellet and the pulp types and the majority of the pellet type took the rice grain form with a size of about 0.5 to 1.5 mm. In the medium into which only phosphate ions were added, the microorganism propagated in the form of very thin pulp and the fluidity of the culture medium substantially decreased. On the other hand, in the culture medium into which magnesium ions, calcium ions, and sodium ions were added, most of the microbial cells took the globular pellet form with a diameter of about 1 to 2 mm, and the result proved to be high in fluidity but low in the lipid content per the microbial cells. However in the culture medium into which all four salts were added, the culture took the form of a mixture of the fine globular pellet and the pulp types, in which fluidity was not deteriorated and a high lipid content was obtained, thereby attaining an enhanced yield of arachidonic acid.

TABLE 3

| Amount of $KH_2PO_4$ added | 0% | 0% | 0.3% (22 mM) | 0.3% (22 mM) |
|---|---|---|---|---|
| Amount of $MgCl_2.6H_2O$ added | 0% | 0.025% (1.2 mM) | 0% | 0.025% (1.2 mM) |
| Amount of $Na_2SO_4$ added | 0% | 0.05% (3.5 mM) | 0% | 0.05% (3.5 mM) |
| Amount of $CaCl_2.2H_2O$ added | 0% | 0.025% (1.7 mM) | 0% | 0.025% (1.7 mM) |
| Amount of arachidonic acid produced | 2.30 g/L | 2.20 g/L | 2.33 g/L | 3.10 g/L |

Example 4

*Mortierella elongata* IFO 8570, *Mortierella exigua* IFO 8571, and *Mortierella hygrophila* IFO 5941 were used as the arachidonic acid-producing microorganisms. Each of six culture media containing 2% glucose, 1.5% edible soy bean protein (manufactured by Ajinomoto Co. Ltd., Es-san Protein SS), 0.1% rapeseed oil and the salts shown in Table 4 in 25 liters was prepared in a 50-liter fermentor, and the initial pH was adjusted to 5.8. An aeration/agitation culture was initiated at 24° C., an aeration rate of 1.0 vvm, an agitation speed of 200 rpm and a fermentor internal pressure of 1.0 kg/cm²G, and the culturing was continued for 7 days. Using the fed-batch method, the glucose concentration was maintained at 1.5% till day 5 and no glucose was added thereafter. Glucose was depleted at the end of culturing for 7 days.

As a result, enhancement in the arachidonic acid yield by salt addition was confirmed.

TABLE 4

| Amount of $KH_2PO_4$ added | 0% | 0.3% (22 mM) |
|---|---|---|
| Amount of $MgCl_2.6H_2O$ added | 0% | 0.05% (2.5 mM) |
| Amount of $Na_2SO_4$ added | 0% | 0.1% (7.0 mM) |
| Amount of $CaCl_2.2H_2O$ added | 0% | 0.05% (3.4 mM) |
| *Mortierella elonciata* IFO 8570 Amount of arachidonic acid produced | 1.50 g/L | 2.20 g/L |
| *Mortierella exiqua* IFO 8571 Amount of arachidonic acid produced | 1.20 g/L | 1.45 g/L |
| *Mortierella hygrophila* IFO 5941 Amount of arachidonic acid produced | 1.25 g/L | 1.45 g/L |

Example 5

*Mortierella alpina* CBS 754.68 was used as an arachidonic acid-producing microorganism. Each of six culture media containing the initial concentrations of 2% glucose, 0.1% soy bean oil and the nitrogen source and the salts shown in Table 5 containing also the added ones by the fed-batch method in 25 liters was prepared in a 50-liter fermentor, and the initial pH was adjusted to 6.0. One hundred milliliters of the liquid precultrue was inoculated thereinto and then was subjected to an aerated agitation culture at 24° C., an aeration rate of 1.0 vvm, an agitation speed of 200 rpm, and a fermentor internal pressure of 200 kPa for 8 days.

Using the fed-batch method, the glucose concentration was maintained at between 1% and 2% till day 4 and at between 0.5% and 1% thereafter. When the nitrogen source was added by the fed-batch method in the middle of culturing, agitation was increased to 300 rpm in the condition Nos. 3 and 4 and to 400 rpm in the condition Nos. 5 and 6 in Table 5 in order to maintain the concentration of dissolved oxygen.

As a result of culturing, increase in the amount of arachidonic acid produced by the addition of salts was confirmed. Furthermore, the effect of salt addition was also confirmed even when a large amount of nutrient sources was added and cultured at relatively high concentrations.

TABLE 5

| Condition No. | 1 | 2 | 3 | 4 | 5 | 6 |
|---|---|---|---|---|---|---|
| Initial amount of soy bean protein | 1.5% | 1.5% | 1.5% | 1.5% | 1.5% | 1.5% |
| Amount of soy bean protein added by fed-batch method during culturing | | | 0.6% | 0.6% | 1.6% | 1.6% |
| Initial amount of $KH_2PO_4$ | | 0.3% (22 mM) | | 0.3% (22 mM) | | 0.3% (22 mM) |
| Initial amount of $MgCl_2.6H_2O$ | | 0.05% (2.5 mM) | | 0.05% (2.5 mM) | | 0.05% (2.5 mM) |
| Initial amount of $Na_2SO_4$ | | 0.1% (7.0 mM) | | 0.1% (7.0 mM) | | 0.1% (7.0 mM) |
| Initial amount of $CaCl_2.2H_2O$ | | 0.05% (3.4 mM) | | 0.05% (3.4 mM) | | 0.05% (3.4 mM) |
| Amount of arachidonic acid produced | 3.60 g/L | 4.90 g/L | 5.00 g/L | 6.81 g/L | 7.32 g/L | 9.04 g/L |

Soy bean protein: tread name; Esusan Meat, product of Ajinomoto Co. Ltd.

Example 6

*Mortierella alpina* SAM1861 (FERM BP-3590) was used as a Mead acid-producing microorganism and *Mortierella alpina* SAM1860 (FERM BP-3589) was used as a dihomo-γ-linolenic acid-producing microorganism. Each of four (2×2 strains) of culture media containing the initial concentrations of 2% glucose, 1.5% soy bean protein (manufactured by Ajinomoto Co. Ltd., Esusan Meat), 0.1% olive oil and the salts shown in Table 6 in 5 liters was prepared in a 10-liter fermentor, and the initial pH was adjusted to 6.0. One hundred milliliters of the liquid precultrue was inoculated thereinto and then was subjected to an aeration/agitation culture at 28° C., an aeration rate of 1.0 vvm, and an agitation speed of 300 rpm for 8 days. The culturing temperature was reduced to 20° C. on day 2. Using the fed-batch method, the glucose concentration was maintained at between 1% and 2%.

As a result, the enhanced yield of Mead acid and dihomo-γ-linolenic acid by the addition of salts was confirmed.

TABLE 6

| Amount of $KH_2PO_4$ added | 0% | 0.3% (22 mM) |
|---|---|---|
| Amount of $MgCl_2.6H_2O$ added | 0% | 0.05% (2.5 mM) |
| Amount of $Na_2SO_4$ added | 0% | 0.1% (7.0 mM) |
| Amount of $CaCl_2.2H_2O$ added | 0% | 0.05% (3.4 mM) |
| *Mortierella alpina* SAM1861 Amount of Mead acid produced | 1.52 g/L | 1.92 g/L |
| *Mortierella alpina* SAM1860 Amount of dihomo-γ-linolenic acid produced | 2.06 g/L | 2.31 g/L |

Example 7

*Mortierella alpina* CBS 754.68 was used as an arachidonic acid-producing microorganism. Six thousand liters of liquid culture medium containing the initial concentrations of 2% glucose, 4% edible soy bean protein, 0.1% soy bean oil, 0.3% $KH_2PO_4$, 0.1% $Na_2SO_4$, 0.05% $MgCl_2.6H_2O$ and 0.05% $CaCl_2.2H_2O$ was prepared in a 10-kiloliter fermentor, and the initial pH was adjusted to 6.1. Thirty liters of the liquid precultrue was inoculated thereinto and then an aeration/agitation culture was initiated at 26° C., an aeration rate of 0.5 vvm, an agitation speed of 30 rpm, and a fermentor internal pressure of 200 kPa. From day 1, culturing was continued with adjusting the aeration rate and the revolving speed to maintain the concentration of dissolved oxygen. Furthermore, 18% glucose was added in several portions from day 1 through day 5 of culturing.

As a result of the aeration/agitation culture for 10 days, the amount of arachidonic acid produced was 13 g/L.

Reference to the microorganisms deposited under Rule 13-2.
The international depository authority
Name: the National Institute of Bioscience and Human-Technology, Agency of Industrial Science and Technology
Address: 1-3, Higashi 1-chome, Tsukuba city, Ibaraki pref., Japan
Mircoorganism (1)
   Name: *Mortierella elongata* SAM 0219
   Deposition date: Mar. 19, 1986
   Deposition number: FERM BP-1239
Mircroorganism (2)
   Name: *Mortierella alpina* SAM 1860
   Deposition date: Sep. 30, 1991
   Deposition number: FERM BP-3589
Microorganism (3)
   Name: *Mortierella alpina* SAM 1861
   Deposition date: Sep. 30, 1991
   Deposition number: FERM BP-3590

What is claimed is:

1. A process for producing unsaturated fatty acids, wherein said unsaturated fatty acid is at least one selected from the group consisting of arachidonic acid, dihomo-γ-linolenic acid, 5,8,11-eicosatrienoic acid and eicosapentaenoic acid, which process comprises culturing a microorganism belonging to the genus Mortierella, wherein the microorganism is selected from the group consisting of *Mortierella alpina, Mortierella elongata, Mortierella exigua* and *Mortierella hygrophila*, in a culture medium containing phosphate ions in the range of 5 to 60 mM, potassium ions in the range of 5 to 60 mM, sodium ions in the range of 2 to 50 mM, magnesium ions in the range of 0.5 to 9 mM, and calcium ions in the range of 0.5 to 12 mM, respectively, to produce said unsaturated fatty acid.

2. The process according to claim 1, wherein the unsaturated fatty add is arachidonic acid.

3. The process according to claim 1, wherein the Mortierella microorganism is selected from the group consisting of *Mortierella exigua* and *Mortierella hygrophila*.

4. A process for producing unsaturated fatty acids, wherein said unsaturated fatty acid is at least one selected from the group consisting of arachidonic acid, dihomo-γ-linolenic acid, 5,8,11-eicosatrienoic acid and eicosapentaenoic acid, which process comprises culturing a microorganism belonging to the genus Mortierella, wherein the microorganism is selected from the group consisting of *Mortierella alpina, Mortierella elongata, Mortierella exigua* and *Mortierella hygrophila*, in a culture medium containing phosphate ions in the range of 10 to 45 mM, potassium ions in the range of 10 to 45 mM, sodium ions in the range of 5 to 40 mM, magnesium ions in the range of 1 to 6 mM, and calcium ions in the range of 1 to 9 mM, respectively, to produce said unsaturated fatty acids.

5. The process according to claim 4, wherein the unsaturated fatty acid is arachidonic acid.

6. The process according to claim 4, wherein the Mortierella microorganism is selected from the group consisting of *Mortierella exigua* and *Mortierella hygrophila*.

7. A process for producing unsaturated fatty acids or a lipid containing said unsaturated fatty acids, which process comprises culturing a microorganism belonging to the genus Mortierella in a medium containing phosphate ions in the range of 5 to 60 mM, potassium ions in the range of 5 to 60 mM, sodium ions in the range of 2 to 50 mM, magnesium ions in the range of 0.5 to 9 mM, and calcium ions in the range of 0.5 to 12 mM, respectively, in the culture medium to produce said unsaturated fatty acids or said lipid containing unsaturated fatty acids, wherein said unsaturated fatty acid is at least one unsaturated fatty acid selected from the group consisting of arachidonic acid, dihomo-γ-linolenic acid, 5,8,11-eicosatrienoic acid and eicosapentaenoic acid, and wherein said Mortierella microorganism is selected from the group consisting of *Mortierella alpina, Mortierella elongata, Mortierella exigua* and *Mortierella hygrophila*.

8. The process according to claim 7, wherein the Mortierella microorganism is selected from the group consisting of *Mortierella exigua* and *Mortierella hygrophila*.

9. A process for producing arachidonic acid or a lipid containing said arachidonic acid, which process comprises culturing a microorganism belonging to the genus Mortierella in a medium containing phosphate ions in the range of 5 to 60 mM, potassium ions in the range of 5 to 60 mM, sodium ions in the range of 2 to 50 mM, magnesium ions in the range of 0.5 to 9 mM, and calcium ions in the range of 0.5 to 12 mM, respectively, in the culture medium to produce said arachidonic acid or said lipid containing arachidonic acid, wherein said Mortierella microorganism is a species selected from the group consisting of *Mortierella alpina, Mortierella elongata, Mortierella exigua* and *Mortierella hygrophila*.

10. The process according to claim 9, wherein the Mortierella microorganism is selected from the group consisting of *Mortierella exigua* and *Mortierella hygrophila*.

11. A process for producing an unsaturated fatty acid or a lipid containing said unsaturated fatty acid, which process comprises culturing a microorganism belonging to the genus Mortierella in a medium containing phosphate ions in the range of 10 to 45 mM, potassium ions in the range of 10 to 45 mM, sodium ions in the range of 5 to 40 mM, magnesium ions in the range of 1 to 6 mM, and calcium ions in the range of 1 to 9 mM, respectively, in the culture medium to produce said unsaturated fatty acid or said lipid containing unsaturated fatty acid, wherein said unsaturated fatty acid is at least one unsaturated fatty acid selected from the group consisting of arachidonic acid, dihomo-γ-linolenic acid, 5,8,11-eicosatrienoic acid and eicosapentaenoic acid, and wherein said Mortierella microorganism is a species selected from the group consisting of *Mortierella alpina, Mortierella elongata, Mortierella exigua* and *Mortierella hydrophila*.

12. The process according to claim, 11, wherein the Mortierella microorganism is selected from the group consisting of *Mortierella exigua* and *Mortierella hygrophila*.

13. A process for producing arachidonic acid or a lipid containing said arachidonic acid, which process comprises culturing a microorganism belonging to the genus Mortierella in a medium containing phosphate ions in the range of 10 to 45 mM, potassium ions in the range of 10 to 45 mM, sodium ions in the range of 5 to 40 mM, magnesium ions in the range of 1 to 6 mM, and calcium ions in the range of 1 to 9 mM, respectively, in the culture medium to produce arachidonic acid or lipid containing arachidonic acid, wherein said Mortierella microorganism is a species selected from the group consisting of *Mortierella alpina, Mortierella elongate, Mortierella exigua* and *Mortierella hygrophila*.

14. The process according to claim 13, wherein the Mortierella microorganism is selected from the group consisting of *Mortierella exigua* and *Mortierella hygrophila*.

* * * * *